United States Patent
Somasundaram et al.

(10) Patent No.: US 7,607,183 B2
(45) Date of Patent: Oct. 27, 2009

(54) BRAKING SYSTEM FOR A POSITIONER IN A MEDICAL IMAGING APPARATUS

(75) Inventors: Baskar Somasundaram, Bangalore (IN); Shaji Alakkat, Bangalore (IN)

(73) Assignee: General Electric Company, Schenectady, NY (US)

( * ) Notice: Subject to any disclaimer, the term of this patent is extended or adjusted under 35 U.S.C. 154(b) by 113 days.

(21) Appl. No.: 11/280,525

(22) Filed: Nov. 15, 2005

(65) Prior Publication Data

US 2007/0107128 A1  May 17, 2007

(51) Int. Cl.
*A61B 6/04* (2006.01)
*B65H 59/10* (2006.01)
(52) U.S. Cl. .............................. 5/601; 378/209; 188/68; 188/139; 192/144
(58) Field of Classification Search ...................... 5/601; 378/209; 192/144; 188/67, 68, 130, 136, 188/139, 156–158
See application file for complete search history.

(56) References Cited

U.S. PATENT DOCUMENTS

| | | | |
|---|---|---|---|
| 4,021,715 A | 5/1977 | Von Hacht et al. | |
| 5,050,202 A | 9/1991 | Yanome | |
| 5,157,707 A | 10/1992 | Ohlson | |
| 5,590,429 A | 1/1997 | Boomgaarden et al. | |
| 5,636,259 A | 6/1997 | Khutoryansky et al. | |
| 5,671,266 A | 9/1997 | Linhart | |
| 5,751,788 A | 5/1998 | Khutoryansky et al. | |
| 5,768,336 A | 6/1998 | Khutoryansky et al. | |
| 5,782,869 A | 7/1998 | Berdut | |
| 5,870,450 A | 2/1999 | Khutoryansky et al. | |
| 5,917,882 A | 6/1999 | Khutoryansky et al. | |
| 6,128,006 A | 10/2000 | Rosenberg et al. | |
| 6,282,264 B1 | 8/2001 | Smith et al. | |
| 6,459,226 B1 | 10/2002 | Zettel et al. | |
| 6,470,519 B1 * | 10/2002 | Pattee et al. | 5/600 |
| 6,769,145 B1 | 8/2004 | Pfeuffer et al. | |
| 6,857,147 B2 * | 2/2005 | Somasundaram | 5/601 |
| 6,952,180 B2 | 10/2005 | Jonsson et al. | |
| 6,986,179 B2 | 1/2006 | Varadharajulu et al. | |
| 7,028,356 B2 | 4/2006 | Somasundaram | |
| 7,177,393 B2 | 2/2007 | Kanemitsu | |
| 2002/0112016 A1 | 8/2002 | Peshkin et al. | |
| 2004/0172758 A1 * | 9/2004 | Alakkat | 5/610 |

FOREIGN PATENT DOCUMENTS

| | | |
|---|---|---|
| EP | 0 765 634 A1 | 2/1997 |
| WO | WO9819744 | 5/1998 |
| WO | 2004049946 A1 | 6/2004 |

OTHER PUBLICATIONS

Biodex Medical Systems, Brachytheratpy Table, http://www.biodex.com/imaging/c_arm/c_arm_810.htrn, Biodex, Shirley New York, USA, Internet site acc'd. Feb. 18, 2006 (3 pp.).
Dornier MedTech :http://www.natco-razi.com.ye/dornier-uro-Lithotripters. htm#Compact%20Delta%20®, Internet site accessed Nov. 11, 2005 (3 pp.).

(Continued)

*Primary Examiner*—Michael Trettel
(74) *Attorney, Agent, or Firm*—William Baxter; Michael G. Smith; Ellis B. Ramirez

(57) ABSTRACT

In one embodiment, a braking system for a positioner unit in a medical imaging apparatus includes a first brake coupled to a drive unit that is configured to drive the positioner unit along an axis susceptible to influence of gravity. A second brake is coupled to the positioner unit, and configured for operating independently of the first brake. Examples of positioner unit include a patient cradle in a patient support table, and a C-arm and a pivot in a vascular gantry.

20 Claims, 4 Drawing Sheets

OTHER PUBLICATIONS

OSI Table: http://www.osiosi.com/pdf/12_16_6864.pdf, OSI, Union City, California, USA, Internet site accessed Nov. 11, 2005 (4 pp.).

Quantum Medical Imaging Table: http://www.quantummedical.net/qv-800.html, Ronkokoma, New York, USA, Internet site accessed Nov. 11, 2005 (3 pp.).

Siemens AG Table: http://energized.esiemenshealthcare.com/urologynews/pdf/Litho_Multi_e.pdf, Munich, Germany, Internet site accessed Nov. 11, 2005 (8 pp.).

Stephanix : http://www.stephanix.com/gb/tele_evoeplus.php, St.-Etienne Cedex 1, France, Internet site accessed Nov. 11, 2005, (2 pp.).

* cited by examiner

BRAKING SYSTEM FOR A POSITIONER IN A MEDICAL IMAGING APPARATUS

FIELD OF THE INVENTION

This invention relates generally to braking systems, and more particularly to, a braking system for a positioner in a medical imaging apparatus.

BACKGROUND OF THE INVENTION

Generally, a positioner in a medical imaging apparatus is used for positioning patients for medical imaging. Examples of a positioner include a patient support table, a vascular gantry comprising a C-arm and a pivot, etc. Examples of a medical imaging apparatus include an X-ray apparatus, a CT scanner, a vascular imaging apparatus, etc.

Typically, the positioner includes a positioner unit and a drive mechanism comprising one or more drive motors for driving the positioner unit along various positioner axes such as, longitudinal, lift and tilt axes. A brake is coupled to the drive mechanism for holding the positioner unit in desired state for positioning a patient for medical imaging. Examples of a positioner unit include a patient cradle in a patient support table, a C-arm and a pivot in a vascular gantry.

However, movement of the positioner unit along the positioner axes such as, for example, lift axis in a vascular gantry, longitudinal axis (in tilted position) in a patient support table, is susceptible to influence of gravity. Moreover, during circumstances such as malfunction in the drive motor, power failure, etc, these axes require a proper braking system for preventing uncontrolled movement of the positioner unit and hence enable safe positioning of the patient for medical imaging.

Known braking systems for a positioner in a medical imaging apparatus include a rotary brake coupled to a drive mechanism corresponding to the positioner axis susceptible to influence of gravity. For example, in the patient support table, the rotary brake is coupled to a shaft of a drive pinion configured to mesh with a rack coupled to a guide mechanism of the patient cradle.

However, during drive along a positioner axis that is susceptible to influence of gravity, if a failure such as a single point failure arises at a location beyond the connection point of the brake and the shaft of the drive pinion, then the operation of the rotary brake does not result in stoppage of patient cradle movement because of the influence of gravity. One example of a single point failure includes teeth breakage in the drive pinion. Thus, conventional braking systems do not allow for sufficiently safe patient positioning for medical imaging, as uncontrolled movement of the positioner unit under the influence of gravity may result in improper patient positioning and may also cause injury to patients during positioning operation.

Thus, there exists a need in the art for a sufficiently safe braking system that would not allow uncontrolled movement of the positioner unit under the influence of gravity, especially during a failure such as, a mechanical failure in the drive mechanism corresponding to a positioner axis that is susceptible to influence of gravity.

SUMMARY OF THE INVENTION

In one embodiment, a braking system for a positioner having a positioner unit, comprises a first brake coupled to a drive unit, the drive unit configured to drive the positioner unit along an axis susceptible to influence of gravity, and a second brake coupled to the positioner unit, wherein the second brake is adapted for operating independently of the first brake.

In another embodiment, a patient support table in a medical imaging apparatus comprises a patient cradle coupled to a guide mechanism, a drive unit coupled to the patient cradle, a first brake coupled to the drive unit, and a second brake coupled to the guide mechanism and configured to operate independently of the first brake.

DETAILED DESCRIPTION OF THE INVENTION

In the following description, reference is made to the accompanying drawings that form a part hereof, and in which is shown by way of illustration specific embodiments that may be practiced. These embodiments are described in sufficient detail to enable those skilled in the art to practice the embodiments, and that it will be appreciated that logical, mechanical, electrical and other changes may be made without departing from the scope of the embodiments. The following detailed description therefore is not to be taken in limiting sense.

Various embodiments of this invention provide a braking system for a positioner in a medical imaging apparatus. However, the embodiments are not limited and may be implemented in connection with various other systems such as, industrial inspection systems, security scanners, etc.

Figure 1:
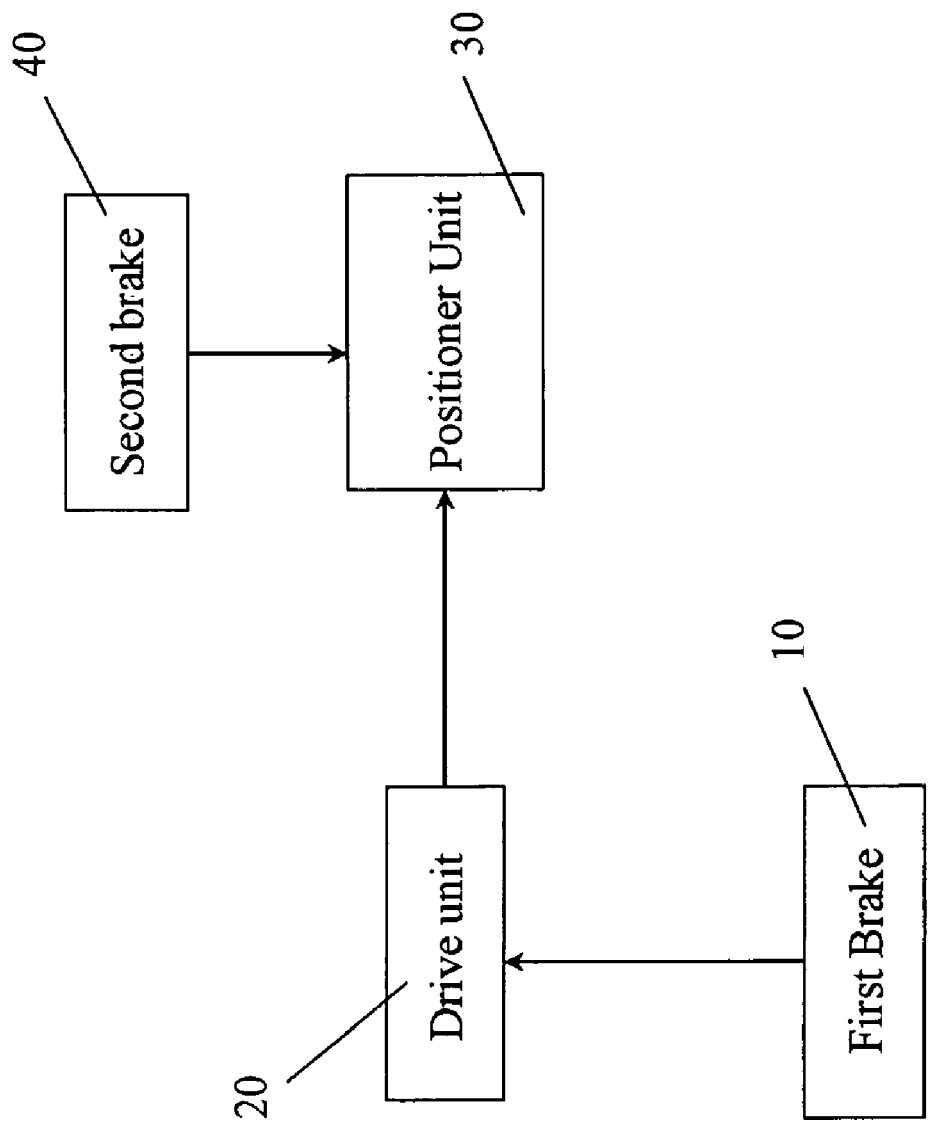
FIG. 1 shows a block diagram of an example of a braking system according to the present invention.

FIG. 1 shows a braking system according to one embodiment of this invention, wherein the braking system includes at least one first brake 10 coupled to a drive unit 20. The drive unit 20 is configured to drive a positioner unit 30 along an axis susceptible to influence of gravity. At least one second brake 40 is coupled to the positioner unit 30. The second brake 40 is configured to operate independently of the first brake 10.

In another embodiment, a processor (not shown) is coupled to the drive unit 20 for operating the second brake 40 in response to a failure in the drive unit 20. This configuration enables automatic holding of the positioner unit 20 by the second brake 40, independently of the first brake 10.

It should be noted that at the time of a failure, e.g., a power failure, or a shear failure occurring at a location beyond a connection point of the first brake 10 with the drive unit 20, the operation of the first brake 10 may not result in stoppage of the movement of the positioner unit 30, especially under the influence of gravity. The configuration of an independently operable second brake 40 according to one embodiment of this invention enables holding of the positioner unit 30 against undesirable movement due to the influence of gravity and also increasing the safety of patients against injury due to uncontrolled movement of positioner unit 30.

In further embodiments, the positioner unit 30 comprises a guide mechanism (not illustrated in FIG. 1) having at least one telescoping member for movement along the axes susceptible to influence of gravity. The second brake 40 is coupled to the telescoping member for holding the positioner unit 30 against influence of gravity during a failure in the drive unit 20.

Examples of a positioner unit 30 include a patient cradle in a patient support table, a C-arm and a pivot in a vascular gantry in a medical imaging apparatus. The axes susceptible to influence of gravity include longitudinal axis in tilted position of the patient cradle, lift axis in a pivot and a gantry.

In further embodiments, the first brake 10 includes a rotary brake and the second brake 40 includes a linear brake. The second brake 40 may further comprise a positive locking configuration in combination with the guide mechanism.

Figure 2:
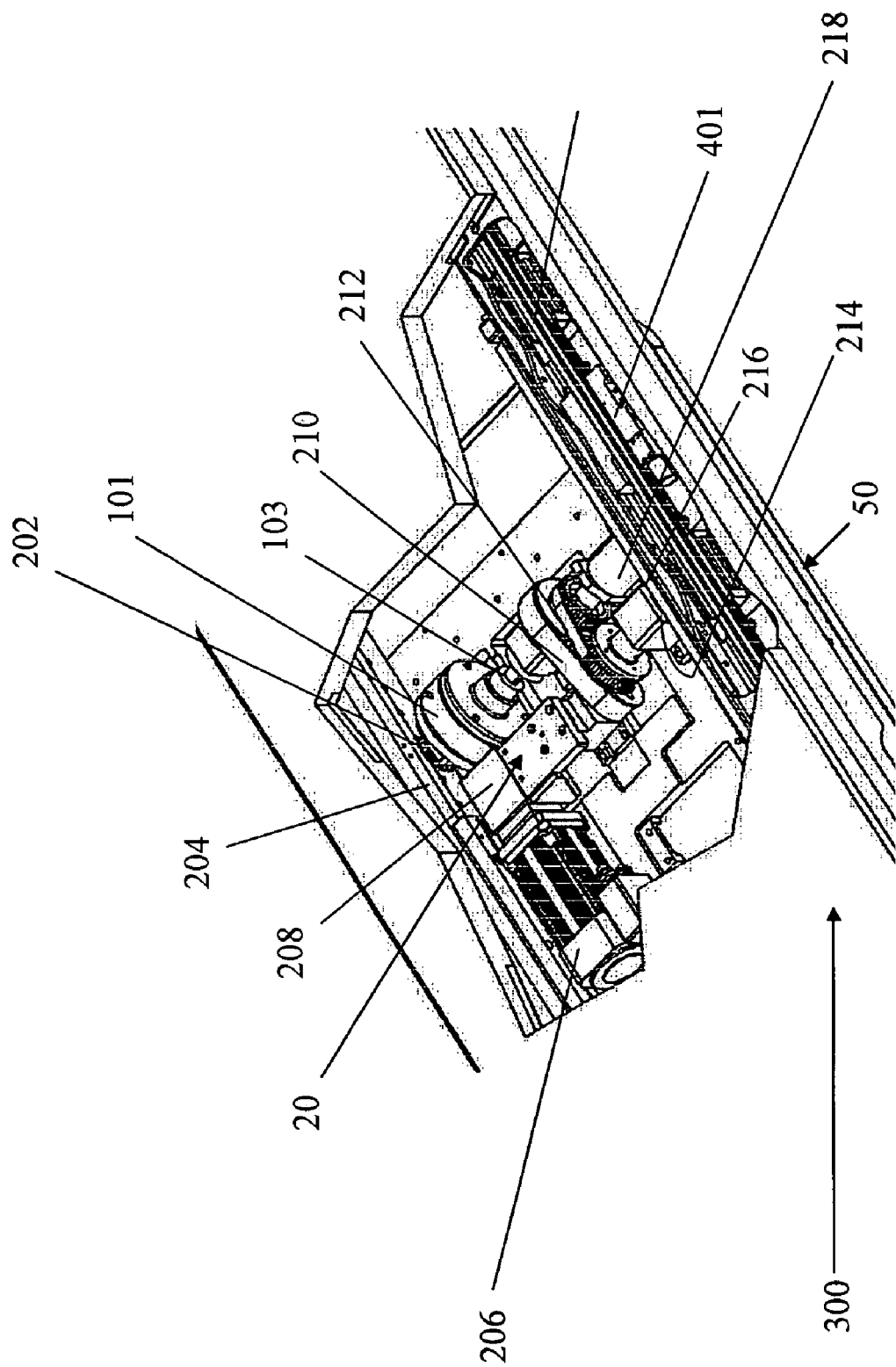
FIG. 2 shows a cut perspective view of a patient support table according to one embodiment of the present invention.

FIG. 2 shows a partial perspective view patient of a support table as an example of a positioner configured with a braking system according to one embodiment of this invention. The patient support table includes a patient cradle 300 configured to move along a guide mechanism 50. A drive unit 20 is coupled to the patient cradle 300. At least one rotary brake 101 is coupled to the drive unit 20. At least one linear brake 401 is coupled to the guide mechanism 50.

One example of the arrangement of the drive unit 20 includes at least one driving member e.g. a drive pinion 202 mounted to a shaft 103, and engageably coupled to a driven member e.g. a main rack 204. The shaft 103 is coupled to a drive motor 206 through a transmission 208 and a main timing belt 210, to transmit the drive from the drive motor 206 to a main rack 204. The main rack 204 is fixedly coupled to the guide mechanism 50, on one side of the patient cradle 300.

Further embodiments of the drive unit 20 may include an auxiliary timing belt 212 coupled to a synchronous pinion 214 for transmitting the drive from the drive motor 206 to a synchronous rack 216 that is fixedly coupled to the guide mechanism 50, on the side of the patient cradle 300, opposite to the main rack 204.

It should be noted that the rotary brake 101, when operated, is configured to hold the shaft 103 of the drive pinion 202 from rotating, and thereby stop the movement of the patient cradle 300 along the guide mechanism 50. In tilted position of the patient cradle 300, for example, at a tilted angle of about 20 degrees, the movement of the patient cradle 300 along the guide mechanism 50 is susceptible to influence of gravity.

Figure 3:
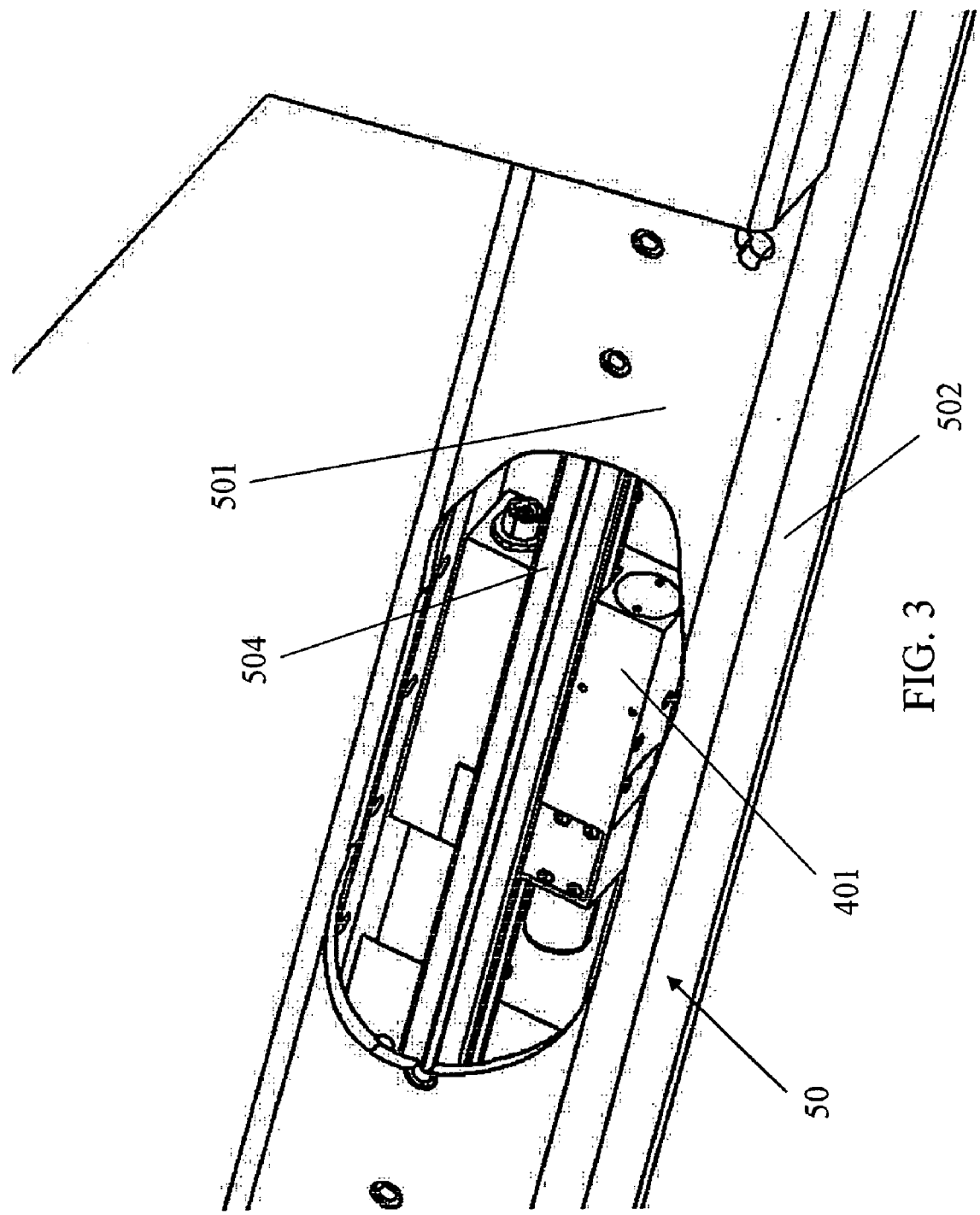
FIG. 3 shows a cut perspective view of an arrangement of the second brake according to one embodiment of the present invention.
Figure 4:
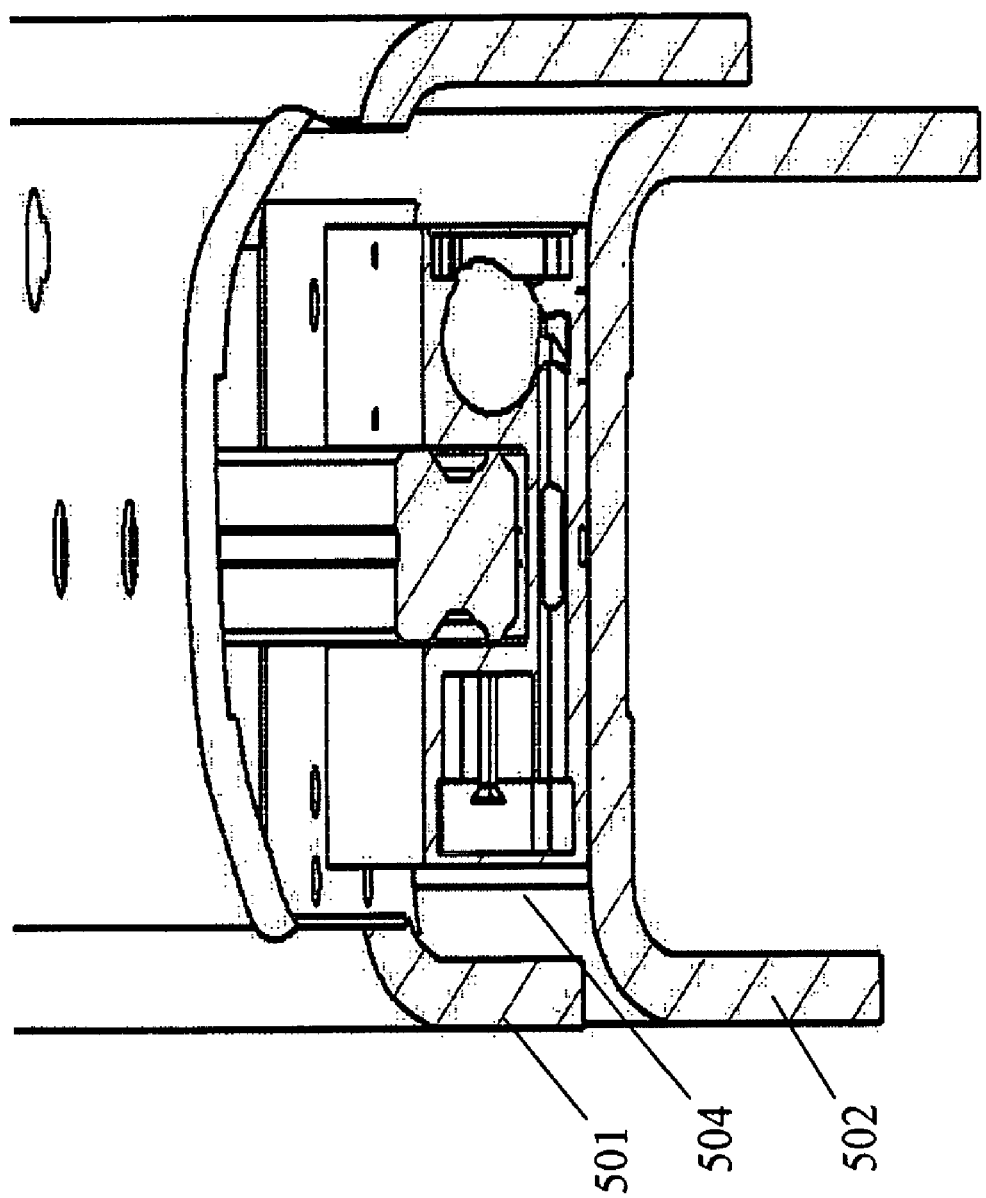
FIG. 4 shows a side cross-section of FIG. 3.

FIG. 3 and FIG. 4 respectively show the perspective and cross section of the arrangement of the linear brake 401 and the guide mechanism 50 according to one embodiment of this invention. Accordingly, the guide mechanism 50 includes at least one telescoping member. An example of a configuration of a telescoping member includes a top channel 501 and a bottom channel 502 coupled through telescoping rails 504. The main rack 204 is fixedly mounted to the top channel 501 and the synchronous rack 216 is fixedly mounted to the bottom channel 502. In this configuration, for every distance moved, say for example, first stage, by the main rack 204, the synchronous rack 216 moves say for example, in second stage, half of the distance moved by the main rack 204 thereby forming a two stage telescoping guide mechanism.

In one embodiment, the linear brake 401 is coupled to the telescoping rails 504. The linear brake includes a known mechanism such as, for example, a manually or automatically operated wedge or a clamp that holds the telescoping rails 504 during a failure and hence prevent the undesirable movement of the patient cradle 300 along the guide mechanism 50 under the influence of gravity.

It should be noted that this configuration also prevents any single point failure in the patient support table by braking at both stages, namely by rotary brake at first stage and the linear brake at second stage and hence prevents patient fall. Disturbance during imaging is avoided as the linear brake 401 and the rotary brake 101 are operated instantaneously to rigidly hold the patient cradle at desired position.

In another embodiment, the linear brake 401 includes a positive locking configuration, wherein the wedge or clamp is configured to hold the telescoping rails 504 against the influence of gravity until the user initiates the movement of the patient cradle 300 during patient positioning operation. This ensures direct braking and increased patient safety in tilted condition of the patient cradle 300.

In further embodiments, a processor e.g. a digital signal processing unit is configured to operate the linear brake 401 and the rotary brake 101 in response to a signal from an encoder (not illustrated).

In one example of operation of the patient support table, the power supply to rotary brake 101 and the linear brake 401 is enabled in response to a command signal from the processor, to release the patient cradle 300, when the user initiates the longitudinal movement of the patient cradle 300. Once the patient cradle 300 reaches desired position by operation of the drive motor 206, the processor issues a command signal to cut off power supply to the drive motor 206 and operate the linear brake 401 and the rotary brake 101 to hold the patient cradle 300 in desired position.

This configuration enables stopping uncontrolled motion in tilted position of the patient cradle 300 due to influence of gravity, in case of a power failure or any malfunction of the drive unit 20. Examples of failure include a mechanical breakage in shaft 103 of the drive pinion 202, belt cut, or a tooth breakage in the drive pinion 202.

It should also be noted that this configuration does not result in loss of longitudinal stroke or reduce compactness of the system, as the linear brake 401 is coupled to the guide mechanism 50. Also, servicing, maintenance, and integration with the processor and encoder are simplified, as the drive unit 20, the linear brake 101 and the linear brake 401 are easily accessible from upper part of the patient cradle 300.

Various embodiments of this invention provide a braking system for a positioner unit in a medical imaging apparatus. Further embodiments of this invention provide a patient support table configured with a braking system that holds patient cradle 300 at two stages.

Thus, the braking system according to various specific embodiments of this invention enables performing a safe patient positioning operation for medical imaging, during circumstances such as, a single point failure that occurs, for example, in the drive unit.

While this invention has been described with various specific embodiments, it will be obvious for a person skilled in the art to practice the invention with modifications. However, all such modifications are have been deemed to be covered within the spirit and scope of the claims appended hereto.

What is claimed is:

1. A braking system comprising:
a first brake coupled to a drive unit;
a guide mechanism unit coupled to the drive unit, wherein the guide mechanism comprises at least one telescoping member;
the drive unit configured to drive the guide mechanism along an axis susceptible to influence of gravity; and
a second brake coupled to the guide mechanism, and configured to operate independently of the first brake, wherein the second brake comprises at least one of a wedge and a clamp to hold the telescoping member against influence of gravity.

2. The braking system according to claim 1, wherein the first brake further comprises at least one rotary brake.

3. The braking system according to claim 1, wherein the drive unit is configured to have at least one driving member driveably coupled to a driven member that is coupled to the guide mechanism, wherein the first brake is coupled to the driving member.

4. The braking system according to claim 1, wherein the drive unit further comprises an auxiliary timing belt.

5. The braking system according to claim 1 further comprising a synchronous rack that is fixedly coupled to the guide mechanism.

6. The braking system according to claim 5, wherein the drive unit further comprises an auxiliary timing belt coupled to a synchronous pinion for transmitting the drive from the drive unit to the synchronous rack.

7. The braking system according to claim 1, wherein the second brake further comprises a positive locking configuration with the telescoping member.

8. The braking system according to claim 6 further comprising at least one a drive pinion mounted to a shaft, and engageably coupled to a main rack.

9. The braking system according to claim 6, further comprising a processor to operate the second brake in response to a failure in the drive unit.

10. The braking system according to claim 1, wherein the positioner further comprises at least one of a patient support table and a vascular gantry.

11. The braking system according to claim 1, wherein the also allowable by virture of dependency on an allowable claim includes at least one of a patient cradle in a patient support table, a C-arm and a pivot in a vascular gantry.

12. A patient support table in a medical imaging apparatus, comprising:

at least a pair of rails configured for moving along an axis susceptible to influence of gravity;

a guide mechanism comprising at least one telescoping member, the telescoping member comprising at least a pair of channels coupled to the at least a pair of rails;

a patient cradle coupled to the guide mechanism;

a drive unit coupled to the patient cradle;

a first brake coupled to the drive unit; and a second brake coupled to the telescoping member of the guide mechanism.

13. The patient support table according to claim 12, further comprising at least one rotary brake in the first brake.

14. The patient support table according to claim 12, further comprising at least one linear brake in the second brake.

15. The patient support table according to claim 12, further comprising a processor to operate the second brake in response to a failure in the drive unit.

16. The patient support table according to claim 12 further comprising a synchronous rack that is fixedly coupled to the guide mechanism.

17. The patient support table according to claim 16, wherein the drive unit further comprises an auxiliary timing belt coupled to a synchronous pinion for transmitting the drive from the drive unit to the synchronous rack.

18. The patient support table according to claim 12, wherein the second brake is coupled to at least the pair of rails.

19. The patient support table according to claim 16 wherein the second brake further comprises a positive locking configuration in combination with the telescoping member.

20. The patient support table according to claim 17 wherein the axis susceptible to influence of gravity includes longitudinal axis in tilted position of the patient cradle.

* * * * *